(12) United States Patent
Blazejewski

(10) Patent No.: US 10,983,330 B2
(45) Date of Patent: Apr. 20, 2021

(54) 3D VIDEO ENDOSCOPE

(71) Applicant: Blazejewski MEDI-TECH GmbH, Sexau (DE)

(72) Inventor: Reinhold Blazejewski, Gutach (DE)

(73) Assignee: Blazejewski MEDI-TECH GmbH, Sexau (DE)

(*) Notice: Subject to any disclaimer, the term of this patent is extended or adjusted under 35 U.S.C. 154(b) by 0 days.

(21) Appl. No.: 16/631,241

(22) PCT Filed: Aug. 3, 2018

(86) PCT No.: PCT/DE2018/100684
§ 371 (c)(1),
(2) Date: Jan. 15, 2020

(87) PCT Pub. No.: WO2019/029772
PCT Pub. Date: Feb. 14, 2019

(65) Prior Publication Data
US 2020/0218057 A1    Jul. 9, 2020

(30) Foreign Application Priority Data
Aug. 8, 2017  (DE) .................... 10 2017 118 035.4

(51) Int. Cl.
  *G02B 23/24*   (2006.01)
  *H04N 13/239*  (2018.01)
  *H04N 5/225*   (2006.01)
  *H04N 7/18*    (2006.01)
  *A61B 1/00*    (2006.01)
  (Continued)

(52) U.S. Cl.
  CPC ....... *G02B 23/2415* (2013.01); *G02B 23/243* (2013.01); *G02B 23/2446* (2013.01);
  (Continued)

(58) Field of Classification Search
  None
  See application file for complete search history.

(56) References Cited

U.S. PATENT DOCUMENTS 5,603,687 A     2/1997 Hori et al.
5,689,365 A *   11/1997 Takahashi .......... A61B 1/00179
                                                    359/362
(Continued)

FOREIGN PATENT DOCUMENTS

DE    10 2008 037 074 A1    2/2010
EP         2310891 B1 *     11/2011
(Continued)

OTHER PUBLICATIONS

International Search Report of PCT/DE2018/100684, dated Nov. 30, 2018.
(Continued)

*Primary Examiner* — Christopher Braniff
(74) *Attorney, Agent, or Firm* — Collard & Roe, P.C.

(57) ABSTRACT

A 3D video endoscope has a shaft which has the form of a flexible or rigid elongated hollow body, a first image sensor, a second image sensor, a first optical channel which comprises a first objective lens and a first optical image guiding system which forwards the image captured by the first objective lens to the first image sensor, a second optical channel which comprises a second objective lens and a second optical image guiding system which forwards the image captured by the second objective lens to the second image sensor. The first optical channel and second optical channel are substantially arranged in the shaft. The first optical channel has a first diaphragm which reduces the aperture of the first optical channel compared to the aperture of the second optical channel. Apart from the first diaphragm, the first optical channel and the second optical channel are structured identically.

15 Claims, 4 Drawing Sheets

Figure 1:
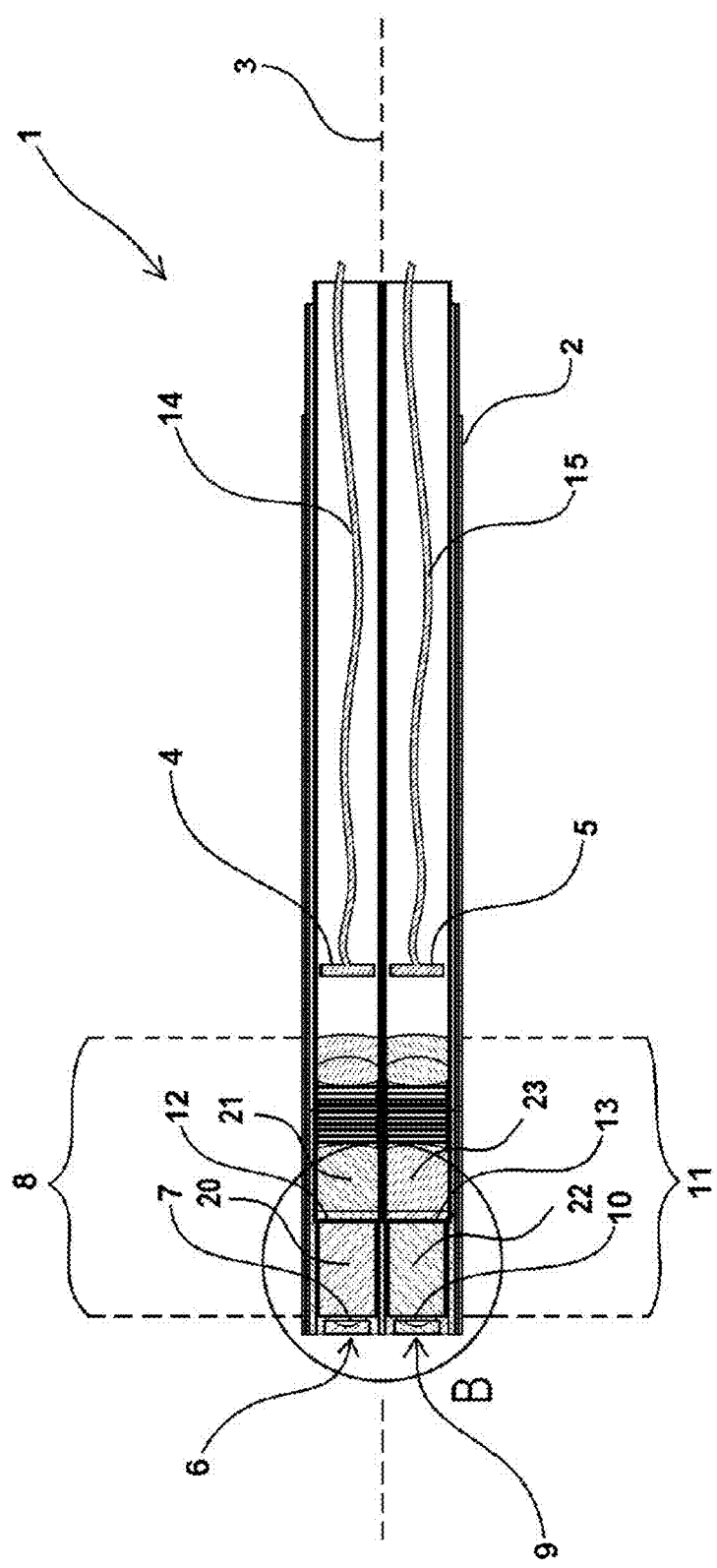

(51) Int. Cl.
  *A61B 1/005*    (2006.01)
  *A61B 1/04*    (2006.01)
(52) U.S. Cl.
  CPC ....... *G02B 23/2484* (2013.01); *H04N 5/2253* (2013.01); *H04N 5/2254* (2013.01); *H04N 7/183* (2013.01); *H04N 13/239* (2018.05); *A61B 1/005* (2013.01); *A61B 1/00078* (2013.01); *A61B 1/00096* (2013.01); *A61B 1/00186* (2013.01); *A61B 1/04* (2013.01)

(56) References Cited

U.S. PATENT DOCUMENTS

| | | | | |
|---|---|---|---|---|
| 2007/0047073 A1* | 3/2007 | Zimmer | ................ | G02B 21/22 |
| | | | | 359/377 |
| 2016/0252721 A1* | 9/2016 | Kuhn | ................ | G02B 23/2415 |
| | | | | 257/432 |
| 2018/0045948 A1 | 2/2018 | Unsai et al. | | |

FOREIGN PATENT DOCUMENTS

| | | |
|---|---|---|
| EP | 3 275 360 A1 | 1/2018 |
| WO | 2017/104191 A1 | 6/2017 |

OTHER PUBLICATIONS

English Translation of the International Preliminary Report on Patentability in PCT/DE2018/100684, dated Jun. 21, 2019.
German Search Report dated Apr. 17, 2018 in German Application No. 10 2017 118 035.4 with English translation of the relevant parts.

\* cited by examiner

3D VIDEO ENDOSCOPE

CROSS REFERENCE TO RELATED APPLICATIONS

This application is the National Stage of PCT/DE2018/100684 filed on Aug. 3, 2018, which claims priority under 35 U.S.C. § 119 of German Application No. 10 2017 118 035.4 filed on Aug. 8, 2017, the disclosures of which are incorporated by reference. The international application under PCT article 21(2) was not published in English.

The invention relates to a 3D video endoscope with a shaft, a first image sensor, a second image sensor, a first optical channel and a second optical channel. The first and second optical channel each comprise an objective lens at the distal end of the shaft and an image guiding system which forwards the image captured by the objective lens to the associated image sensor.

Video endoscopes are used both in the technical and the medical sector. They are used to examine structures on the surface or in difficult to access cavities, channels or recesses. The naked eye is often insufficient to resolve these structures. In the medical sector, video endoscopes are used in minimally invasive surgery for examination purposes or in combination with surgical instruments for operations under visual inspection. A lighting system can be used to illuminate the structures to be examined. The light generated by an external light source is usually transmitted to the structure to be examined via optical fibres. An imaging system is used to capture the information that is contained in the light reflected by the structure as an image. An image converter chip, such as CMOS or CCD, is frequently used as the camera or image sensor. The image sensor, also called an image generator, converts the optical signals into electrical signals which are then made optically visible on a screen or a monitor.

There are various methods and devices for providing the user with the most concrete impression from the location of the distal end of the endoscope. The images generated by the 3D video endoscope are displayed for a user on a display unit, e.g. on a monitor or screen. The images are shown on the display unit so that the viewer obtains a three-dimensional impression of the location. A screen shows separate images for the left and right eye of the viewer. The viewer generally requires special glasses so that the images intended for the viewer's left eye are only perceived by the left eye and the images intended for the viewer's right eye are only perceived by the right eye. These include for example polarised glasses, colour filter glasses, interference filter glasses and LCD shutter glasses. There are also special display units that the viewer arranges on his head in the direct vicinity of his eyes. These type of display units are integrated into a 3D headset, for example. They are also referred to as 3D video glasses and are equipped with two displays.

On known endoscopes for the generation of three-dimensional depictions the image generator or generators are arranged at the proximal or distal end. The endoscope generally contains a flexible or rigid shaft which takes the form of an elongated hollow body. The light reflected by a structure to be examined is input at the distal end via a first objective lens and a second objective lens and fed via two spatially separate optical systems with optical components such as lenses and prisms or through an optical fibre to the image generator or generators. The image generators are referred to as image sensors. A first optical channel contains the first objective lens at the distal end of the shaft and a first optical image guiding system. The first optical image guiding system forwards the image captured by the first objective lens to the first image sensor. A second optical channel contains the second objective lens at the distal end of the shaft and a second optical image guiding system. The second optical image guiding system forwards the image captured by the second objective lens to the second image sensor. The first and second objective lens are the same size and are arranged adjacent to one another at the distal end of the shaft. The first and second optical channel are generally identical. The images captured by the image sensors are combined by image processing equipment to form a three-dimensional image and visually displayed for the user on a display unit.

If the 3D endoscope is to be used for the examination of structures in small cavities, the diameter of the shaft must be as small as possible and in particular smaller than the cavity into which the endoscope is to be introduced. With a small shaft diameter, the distance between the first objective lens and the second objective lens is small. The maximum possible overlap area of the visual fields of both objective lenses must be guaranteed here despite the small distance between the objective lenses as a three-dimensional depiction of the structures is only possible in the overlap area. Furthermore, a small shaft diameter results in the necessity of the diameter of the first and second objective lenses being small, in particular smaller than the radius of the shaft. The free opening or opening width of the first and second channel is referred to as the aperture. The aperture of the first and second channel influences the brightness and the depth of field. If the aperture is small, there is less brightness but a large depth of field. If the aperture is increased, the brightness increases but the depth of field decreases. Should there be the intention to improve the depth of field with a specified shaft diameter of a known 3D video endoscope, this is generally achieved by decreasing the aperture of the first optical channel and the second optical channel, for example in that a diaphragm is inserted in both the first and the second channel. This has the disadvantage, however, of reducing the overall brightness.

The invention is based on the task of providing a 3D video endoscope that has a shaft with a small diameter for the examination of small cavities and with which images are generated that have a greater depth of field compared to known 3D video endoscopes without resulting in a reduction of the brightness, whereby the endoscope is comprised of optical components in such a manner that a special adjustment of the depth of field and the brightness to the specific application is possible with little effort during the production of the endoscope.

This object is achieved by a 3D video endoscope having the features of Claim 1. It is characterised in that the two optical channels have a different aperture. The first optical channel has a smaller aperture than the second optical channel. This means that the free opening of the first channel for incident light is smaller than the free opening of the second optical channel. The term opening width can also be used in place of free opening. The images that are generated by the first image sensor are referred to as the first images. The images that are generated by the second image sensor are referred to as the second images. The depth of field of the images created with the first image sensor is thus greater than the depth of field of the images created with the second image sensor. This means that the area that is shown in focus with the first optical channel on the first image sensor is greater than the area that is shown in focus with the second optical channel on the second image sensor. In contrast, the brightness of the second images is greater than the brightness of the first images. An image processing equipment combines the first images and the second images to create three-dimensional images. These three-dimensional images are processed such that they essentially exhibit the brightness of the second images and the depth of field of the first images. Compared to the three-dimensional images of known 3D video endoscopes, the three-dimensional images of the 3D video endoscope according to the invention have the advantage that they have better depth of field and comparable brightness.

The first image sensor and second image sensor can be two separate image generators. As an alternative, the first image sensor and the second image sensor can be part of a single image generator. The image generator can be an image converter chip, for example. A first portion of the pixels from the image converter chip are assigned to the first image sensor and the second portion of the pixels to the second image sensor.

The first channel is equipped with a first diaphragm which reduces the aperture of the first channel compared to the aperture of the second channel. The first diaphragm can be assigned to any desired position within the first channel. The diaphragm opening can be round, for example. Or the diaphragm opening can be square instead. Star-shaped diaphragm openings are also possible. And crescent-shaped diaphragm openings are conceivable.

The aperture of the first optical channel is reduced by the first diaphragm. The first optical channel and the second optical channel are structured identically apart from the first diaphragm. The first objective lens and the second objective lens have the same diameter. Furthermore, the other optical components of the first optical channel and of the second optical channel have the same diameter, in particular the same outer diameter. The only difference between the first and second optical channel thus lies in the diaphragm. As both optical channels are structured identically, production of the endoscope is thus made correspondingly easier. In the first optical channel, depending on the depth of field and brightness specified by the application a first diaphragm with the corresponding diaphragm opening is inserted. A corresponding adjustment of the endoscope to the application requires little effort.

According to an advantageous embodiment of the invention, the diaphragm is an aperture diaphragm. It can also be referred to as an aperture stop.

According to a further advantageous embodiment of the invention, the first diaphragm is a pinhole. The opening of the pinhole is specified as the diaphragm opening.

According to a further advantageous embodiment of the invention, the first diaphragm is arranged within the first optical channel between the first objective lens and the first image sensor.

According to a further advantageous embodiment of the invention, the first diaphragm is arranged on the first objective lens on the side facing away from the first image sensor. The first diaphragm is thus located at the outlet of the first objective lens. It is part of the first optical channel.

According to a further advantageous embodiment of the invention, the first diaphragm has the form of a pinhole which is arranged at one of the optical components of the first optical channel. The pinhole can be adhered or puttied on at the objective lens or an optical component arranged adjacent to the objective lens. Furthermore, it is possible that the pinhole is applied directly as a coating on one of the optical components of the first optical channel.

According to a further advantageous embodiment of the invention, the second optical channel is equipped with a second diaphragm whose diaphragm opening is larger than the diaphragm opening of the first diaphragm and the first optical channel and the second optical channel are structured identically apart from the first diaphragm and the second diaphragm. In this case, the first optical channel and the second optical channel are each equipped with a diaphragm. Both diaphragms can have the same qualities. For example, the first diaphragm and the second diaphragm can both be diaphragms with a circular opening. The first and second diaphragm differ in terms of the size of the opening, however. Apart from the first and second diaphragm, the first optical channel and the second optical channel can be structured identically.

According to a further advantageous embodiment of the invention, the second diaphragm is an aperture diaphragm and in particular a pinhole.

According to a further advantageous embodiment of the invention, the second diaphragm is arranged within the second optical channel between the second objective lens and the second image sensor.

According to a further advantageous embodiment of the invention, the second diaphragm is arranged on the second objective lens on the side facing away from the second image sensor. The second diaphragm is thus located at the outlet of the second objective lens. The second diaphragm is part of the second optical channel.

According to a further advantageous embodiment of the invention, the second diaphragm has the form of a pinhole which is arranged at one of the optical components of the second optical channel.

According to a further advantageous embodiment of the invention, the first optical channel is equipped with a lens which additionally decreases the aperture of the first channel compared to the aperture of the second channel. This can be any lens of the first optical channel. It can either be additionally mounted in the first optical channel otherwise structured identically to the second optical channel or it can replace a different lens. In the latter case, it is beneficial for the lens to have identical optical properties, apart from the aperture, as the lens that it is replacing and as the corresponding lens in the second optical channel.

According to a further advantageous embodiment of the invention, the first image sensor and the second image sensor are arranged in the shaft.

According to a further advantageous embodiment of the invention, the first image sensor and the second image sensor are arranged outside the shaft.

According to a further advantageous embodiment of the invention, the first channel has a different f-number than the second channel. The f-number is also referred to as the f-stop. This is the ratio between focal length and the diameter of the effective entrance pupil. These is particularly true for the first and second objective lens. The diameter of the effective entrance pupil determines the aperture. If the first optical channel has a smaller aperture than the second optical channel, the f-number of the first optical channel and the f-number of the second optical channel are different at the same focal length.

According to a further advantageous embodiment of the invention, the f-number of the first channel is greater than the f-number of the second channel.

According to a further advantageous embodiment of the invention, the 3D video endoscope is equipped with image processing equipment which uses the first images that the first image sensor generates and the second images that the second image sensor generates to create three-dimensional images, and which during the creation of the three-dimensional images adopts the brightness of the second images generated with the second image sensor and the depth of field of the first images generated with the first image sensor. It is beneficial to take the contrast into account during the generation of the three-dimensional images. Preferably individual pixels of the first and second image generator are specifically selected here. It would be best to use a FPGA for this.

Further advantages and advantageous embodiments of the invention can be obtained from the following description, the drawing and the claims.

DRAWING

The drawing shows a model embodiment of the invention. Illustrations:

FIG. 1 3D video endoscope in a longitudinal section

Figure 2:
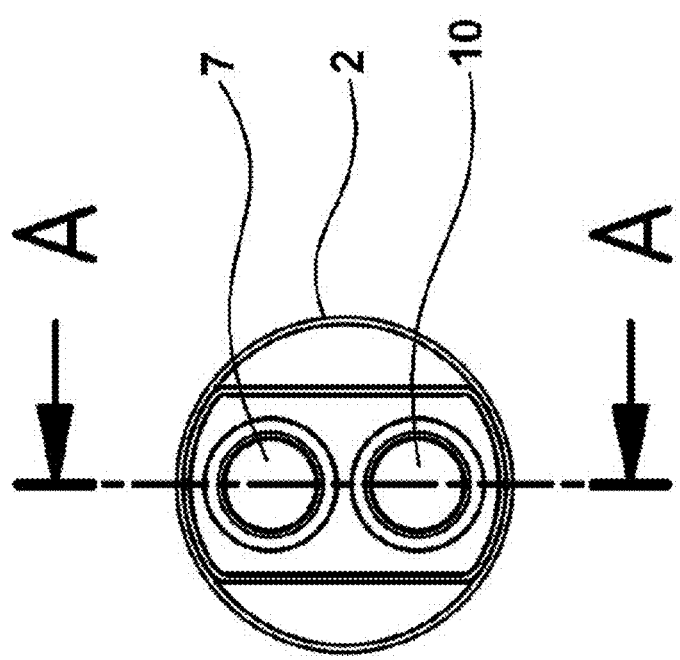

FIG. 2 3D video endoscope according to FIG. 1 in a view from the front

Figure 3:
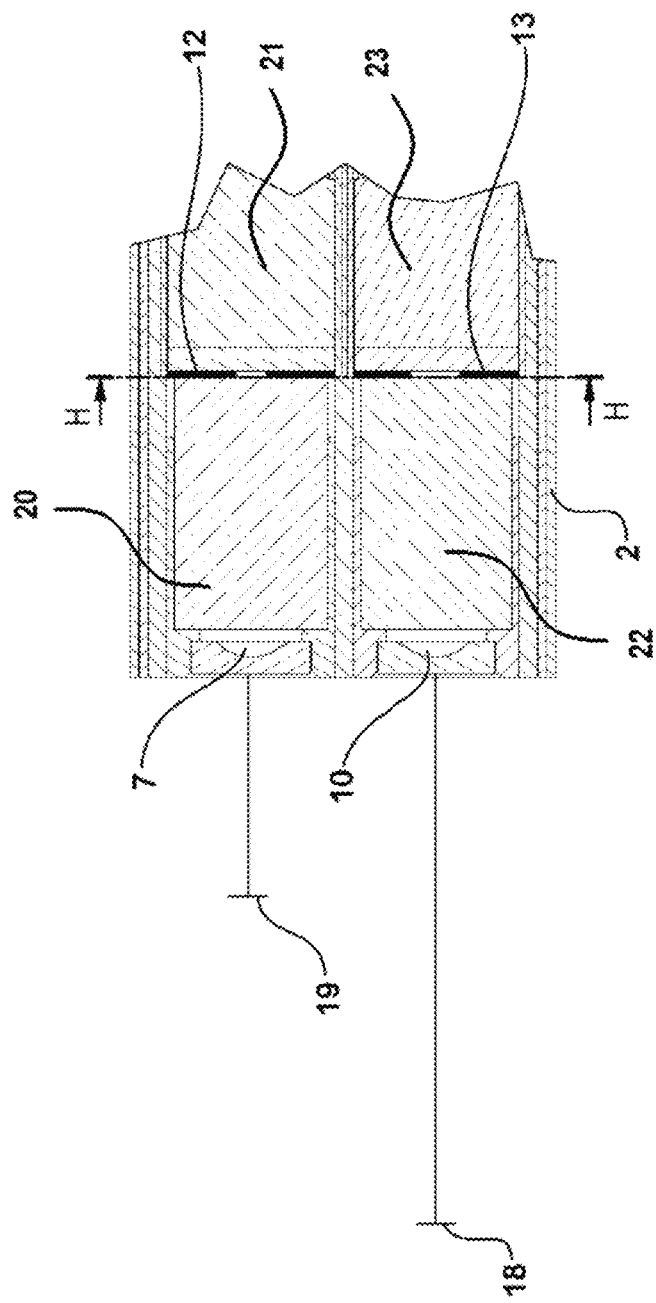

FIG. 3 Detail from FIG. 1

Figure 4:
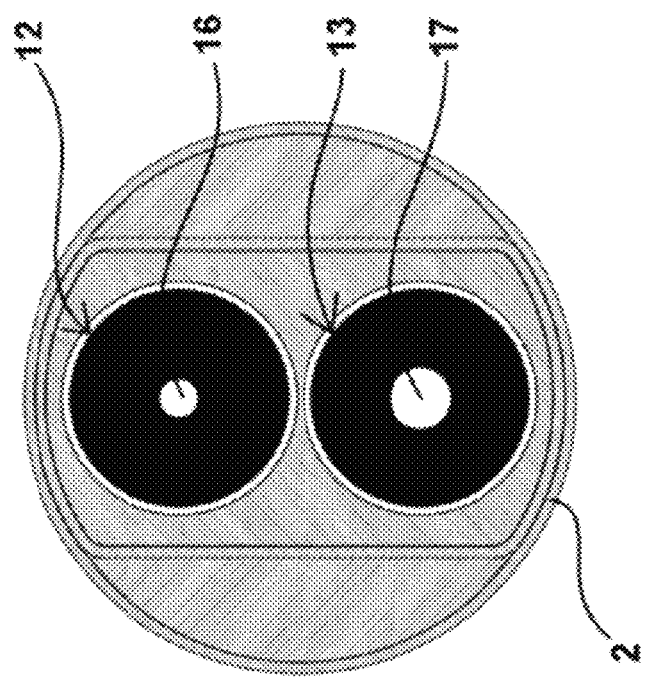

FIG. 4 Cross-section through the 3D video endoscope according to FIG. 1 along the level designated with H-H in FIG. 3.

DESCRIPTION OF THE MODEL EMBODIMENT

FIGS. 1 to 4 represent a model embodiment of a 3D video endoscope 1. The 3D video endoscope has an elongated shaft 2 that runs along a longitudinal axis 3. A first image sensor 4 and a second image sensor 5 are arranged adjacent to one another in the shaft 2. The two image sensors are connected via signal lines 14 and 15 with an image processing equipment not shown in the drawing. A first optical channel 6 is assigned to the first image sensor 4. The first optical channel 6 contains the first objective lens 7 at the distal end of the shaft 2 and a first optical image guiding system 8. The first optical image guiding system 8 forwards the image captured by the first objective lens 7 to the first image sensor 4. The distal end of the shaft 2 is located on the left side in FIG. 1. The proximal end of the shaft 2 is located on the right side in FIG. 1. A second optical channel 9 is assigned to the second image sensor 5. A second optical channel 9 contains a second objective lens 10 at the distal end of the shaft 2 and a second optical image guiding system 11. The second optical image guiding system 11 forwards the image captured by the second objective lens 10 to the second image sensor 5. The first and second image guiding system 8, 11 comprise several lenses as optical components.

A first diaphragm 12 is arranged in the first optical image guiding system 8. A second diaphragm 13 is arranged in the second optical image guiding system 11. Both diaphragms 12, 13 are shown in FIG. 3. Furthermore, both diaphragms 12, 13 are identifiable in FIG. 4 in a top view. FIG. 4 shows a cross-section through the 3D video endoscope along the level designated with H-H in FIG. 3 in which both diaphragms 12, 13 are arranged. The outer diameter of both diaphragms 12, 13 is the same. Both diaphragms 12, 13 have a circular diaphragm opening 16, 17. They are designed as aperture diaphragms, in particular as pinholes. The two diaphragms 12, 13 differ in the size of the diaphragm opening. The diaphragm opening 16 of the first diaphragm 12 is smaller than the diaphragm opening 17 of the second diaphragm 13. The size of the diaphragm opening determines the brightness of the images generated with the first and second optical channel. As the diaphragm opening 17 of the second diaphragm 13 is larger than the diaphragm opening 16 of the first diaphragm 12, the brightness of the images generated with the second optical channel is greater than the brightness of the images generated with the first channel.

The first diaphragm 12 with its diaphragm opening 16 determines the aperture of the first optical channel 6, as all other components of the first optical channel 6 have a larger opening width than the first diaphragm 12. The same applies for the second diaphragm: the second diaphragm 13 determines with its diaphragm opening 17 the aperture of the second optical channel, as all other components of the second optical channel have a larger opening width than the second diaphragm 13.

The first objective lens 7 and the second objective lens 10 have the same diameter. All optical components of the first optical channel and all optical components of the second optical channel generally have the same outer diameter. This also applies for the first and second diaphragm 12, 13. The only difference between the first optical channel 6 and the second optical channel 9 exists with regard to the diaphragm opening 16 of the first diaphragm 12 and the diaphragm opening 17 of the second diaphragm 13.

In the first optical channel 6 the first objective lens 7 is connected to a first glass rod 20. The first diaphragm 12 is secured on the end of the first glass rod 20 facing away from the first objective lens 6. It is glued onto the first glass rod 12. Another glass rod 21 follows the first diaphragm 12 in the direction of the first image sensor 4.

The same applies to the second optical channel 9. In the second optical channel 9 the second objective lens 10 is connected to a second glass rod 22. The second diaphragm 13 is secured on the end of the second glass rod 22 facing away from the second objective lens 10. It is glued onto the second glass rod 22. Another glass rod 23 follows the second diaphragm 13 in the direction of the second image sensor 5.

FIG. 2 shows the 3D video endoscope 1 in a view from the front on the distal end. In this depiction the shaft 2, the first objective lens 7 and the second objective lens 10 are identifiable. Furthermore, the level A-A is marked in FIG. 2, along which the 3D video endoscope is depicted in a longitudinal section in FIG. 1.

FIG. 3 shows the detail from FIG. 1 marked with B in FIG. 1. The first objective lens 7 and the first diaphragm 12 of the first optical channel 6 and the second objective lens 10 and the second diaphragm 13 of the second optical channel are identifiable. The first objective lens 7 and the second objective lens 10 have the same focal length. Overall the focal length of the first optical channel 6 is identical to the focal length of the second optical channel 9. The aperture of the first optical channel dictated by the diaphragm opening 16 of the first diaphragm 12 is smaller than the aperture of the second optical channel dictated by the diaphragm opening 17 of the second diaphragm 13. The f-stop is the ratio between focal length and aperture. As a result, the f-stop of the first optical channel 6 is greater than the f-stop of the second optical channel 9. The left side of FIG. 3 shows the areas for the first optical channel and the second optical channel which are shown in focus on the first image sensor 4 and on the second image sensor 5. The first optical channel has a smaller aperture than the second optical channel due to the smaller diaphragm opening 16 of the first diaphragm 12. As a result, the depth of field of the first optical channel is greater than the depth of field of the second optical channel. The area of the first optical channel shown in focus begins in FIG. 3 at the position marked with the reference number 19 and extends to the left starting from position 19. The area of the second optical channel shown in focus begins in FIG. 3 at the position marked with the reference number 18 and extends to the left starting from this position. Both areas extend approximately the same distance to the left. The second end of the areas of the first and second channel shown in focus is not shown in the drawing. As a result, the area for the first optical channel 6 shown in focus starts closer to the first objective lens 7 than the area for the second optical channel 9 shown in focus, which starts at a greater distance to the second objective lens 10. Because the area of the first optical channel shown in focus and the area of the second optical channel shown in focus extend about the same distance to the left, the area of the first optical channel shown in focus is larger than the area of the second optical channel shown in focus. The depth of field of the first optical channel is thus greater than the depth of field of the second optical channel.

All features of the invention can be material to the invention both individually and in any combination.

REFERENCE NUMBERS 1 3D video endoscope
2 Shaft
3 Longitudinal axis
4 First image sensor
5 Second image sensor
6 First optical channel
7 First objective lens
8 First image guiding system
9 Second optical channel
10 Second objective lens
11 Second image guiding system
12 First diaphragm
13 Second diaphragm
14 Signal line
15 Signal line
16 Diaphragm opening of the first diaphragm
17 Diaphragm opening of the second diaphragm
18 Beginning of the area of the second optical channel shown in focus
19 Beginning of the area of the first optical channel shown in focus
20 First glass rod
21 Glass rod
22 Second glass rod
23 Glass rod

The invention claimed is:

1. A 3D video endoscope, comprising:
a shaft (2) which has the form of a flexible or rigid elongated hollow body with a longitudinal axis (3) running in the longitudinal direction,
a first image sensor (4) and a second image sensor (5),
a first optical channel (6) which comprises a first objective lens (7) at a distal end of the shaft and a first optical image guiding system (8) which forwards an image captured by the first objective lens (7) to the first image sensor (4),
a second optical channel (9) which comprises a second objective lens (10) at the distal end of the shaft and a second optical image guiding system (11) which forwards an image captured by the second objective lens (10) to the second image sensor (5),
wherein the first optical channel (6) and second optical channel (9) are substantially arranged in the shaft (2),
wherein the aperture of the first optical channel (6) is smaller than the aperture of the second optical channel (9),
wherein the first optical channel (6) is equipped with a first diaphragm (12) which reduces the aperture of the first optical channel (6) compared to the aperture of the second optical channel (9),
wherein the first diaphragm (12) is a pinhole,
wherein apart from the first diaphragm (12) the first optical channel (6) and the second optical channel (9) are structured identically such that the first objective lens (7) has the same diameter as the second objective lens (10) and the first optical image guiding system (8) and the second optical image guiding system (11) have the same outer diameter, and
wherein the 3D video endoscope is equipped with an image processing equipment which uses the first images that the first image sensor (4) generates and the second images that the second image sensor (5) generates to create three-dimensional images, and which during the creation of the three-dimensional images adopts the brightness of the second images generated with the second image sensor (5) and the depth of field of the first images generated with the first image sensor (4).

2. The 3D video endoscope according to claim 1, wherein the first diaphragm (12) is an aperture diaphragm.

3. The 3D video endoscope according to claim 1, wherein the first diaphragm (12) is arranged within the first optical channel (9) between the first objective lens (7) and the first image sensor (4).

4. The 3D video endoscope according to claim 1, wherein the first diaphragm (12) is arranged at the first objective lens (7) on the side facing away from the first image sensor (4).

5. The 3D video endoscope according to claim 3, wherein the first diaphragm (12) has the form of a pinhole and is arranged at one of the optical components of the first optical channel (6).

6. The 3D video endoscope according to claim 1, wherein the second optical channel (9) is equipped with a second diaphragm (13) and wherein a diaphragm opening (16) of the first diaphragm (12) is smaller than a diaphragm opening (17) of the second diaphragm (13) and wherein the first optical channel (6) and the second optical channel (9) are structured identically apart from the first diaphragm (12) and the second diaphragm (13).

7. The 3D video endoscope according to claim 6, wherein the second diaphragm (13) is an aperture diaphragm.

8. The 3D video endoscope according to claim 6, wherein the second diaphragm (13) is arranged within the second optical channel (9) between the second objective lens (10) and the second optical image sensor (5).

9. The 3D video endoscope according to claim 6, wherein the second diaphragm (13) is arranged at the second objective lens (10) on the side facing away from the second image sensor (5).

10. The 3D video endoscope according to claim 8, wherein the second diaphragm (13) has the form of a pinhole and is arranged at one of the optical components of the second optical channel (9).

11. The 3D video endoscope according to claim 1, wherein the first optical channel (6) is equipped with a lens which additionally decreases an aperture of the first optical channel compared to an aperture of the second optical channel (9).

12. The 3D video endoscope according to claim 1, wherein the first image sensor (4) and the second image sensor (5) are arranged in the shaft (2).

13. The 3D video endoscope according to claim 1, wherein the first image sensor and the second image sensor are arranged outside the shaft.

14. The 3D video endoscope according to claim 1, wherein the first optical channel (6) has a different f-number, also called f-stop, than the second optical channel (9).

15. The 3D video endoscope according to claim 14, wherein the f-number of the first optical channel (6) is greater than the f-number of the second optical channel (9).

* * * * *